United States Patent [19]

Franz et al.

[11] 4,211,548

[45] Jul. 8, 1980

[54] ESTERS OF N-PHOSPHINOTHIOYLMETHYLGLYCINE AND HERBICIDAL METHOD

[75] Inventors: John E. Franz, Crestwood; Robert J. Kaufman, University City, both of Mo.

[73] Assignee: Monsanto Company, St. Louis, Mo.

[21] Appl. No.: 974,184

[22] Filed: Dec. 26, 1978

[51] Int. Cl.$^2$ .......................... C07F 9/40; A01N 9/36
[52] U.S. Cl. ........................................ 71/87; 260/941
[58] Field of Search ............................ 71/87; 260/941

[56] References Cited

U.S. PATENT DOCUMENTS

| | | | |
|---|---|---|---|
| 3,799,758 | 3/1974 | Franz | 71/86 |
| 3,991,095 | 11/1976 | Gaertner | 71/86 |
| 4,067,719 | 1/1978 | Dutra | 71/87 |
| 4,120,689 | 10/1978 | Dutra | 71/87 |

FOREIGN PATENT DOCUMENTS 1000655  8/1965  United Kingdom ........................ 71/87

*Primary Examiner*—Anton H. Sutto
*Attorney, Agent, or Firm*—William T. Black; Donald W. Peterson

[57] ABSTRACT

This disclosure relates to a new class of organic chemical compounds. More particularly, this disclosure is concerned with ester derivatives of N-phosphinothioylmethylglycine wherein the phosphorus atom is attached to a divalent sulfur atom and the strong acid salts thereof. This class of compounds has been found to display desirable herbicidal activity when applied to certain varieties of weeds or undesired plants.

36 Claims, No Drawings

ESTERS OF N-PHOSPHINOTHIOYLMETHYLGLYCINE AND HERBICIDAL METHOD

This invention relates to a new class of organic chemical compounds. More particularly, this invention is concerned with ester derivatives of N-phosphinothioylmethylglycine wherein ester or thioester groups are bonded to the phosphorus atom in addition to a divalent sulfur atom. This class of compounds has been found to display desirable herbicidal activity when applied to certain varieties of weeds or undesired plants.

U.S. Pat. No. 3,799,758 describes the preparation of N-phosphonomethylglycine and certain of its esters, amides and salts. Also described is the use of such compounds as contact or post-emergent herbicides.

U.S. Pat. No. 3,991,095 describes derivatives of N-phosphonomethylglycine and salts thereof wherein there is a thiocarbonyl group attached to the nitrogen atom.

U.S. patent application Ser. No. 922,900 filed July 10, 1978 describes certain thioester derivatives of N-trifluoroacetyl-N-phosphonomethylglycine.

It will be apparent from a study of the above patents that none of them disclose or suggest phosphonomethylglycines containing a P=S grouping.

The compounds of the present invention are represented by the formula

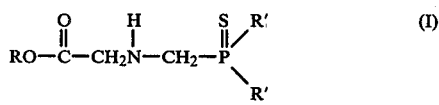

wherein R is a member of the class consisting of alkyl of from 1 to 10 carbon atoms, chloroalkyl of from 1 to 4 carbon atoms and from 1 to 3 chlorine atoms and alkoxyalkyl containing from 3 to 7 carbon atoms and each R' is a member of the class consisting of thioalkyl of from 1 to 6 carbon atoms, phenoxy, phenylthio and substituted phenoxy and phenylthio having 1 to 2 substituents selected from the class consisting of halo, lower alkyl and lower alkoxy and the strong acid salts thereof. It is preferred that R be alkyl or chloroalkyl of from 1 to 4 carbon atoms. It is even more preferred that R be methyl, ethyl or monochloroethyl. It is preferred that R' represent phenylthio, halophenylthio or alkylthio of from 1 to 4 carbon atoms. It is even more preferred that R' represent alkylthio of from 1 to 4 carbon atoms.

Illustrative of the alkyl groups represented by R are methyl, ethyl, n- and isopropyl, n-, sec-, iso- and tert-butyl, pentyl, hexyl, octyl and decyl. The chloroalkyl groups that R represents are, for example, chloromethyl, chloroethyl, chloropropyl, trichloropropyl, chlorobutyl and the like.

Illustrative of the alkoxyalkyl groups which R represents are methoxyethyl, methoxypropyl, methoxybutyl, ethoxyethyl, ethoxypropyl, propoxyethyl, propoxypropyl and the like.

The substituted phenoxy and phenylthio groups which R' represents are, for example, halogen-substituted groups such as chlorophenoxy, bromophenoxy, iodophenylthio, fluorophenylthio, dichlorophenylthio, dibromophenylthio, chlorobromophenoxy and the like, tolyloxy, ethylphenylthio, butylphenylthio, methoxyphenylthio, methylchlorophenoxy, ethylbromophenylthio, ethoxyphenylthio, butoxyphenoxy, and the like.

In accordance with the present invention, the compounds of formula (I) are prepared by reacting a compound of the formula

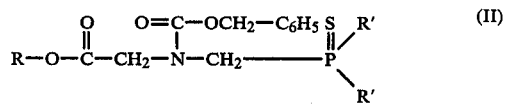

wherein R and R' are as above defined with hydrogen bromide in a solvent such as glacial acetic acid at a temperature of from −10° C. to about +30° C. and then treating the resultant product believed to be the hydrobromide salt with propylene oxide in the presence of an aprotic solvent such as benzene, toluene and the like.

The aprotic solvents employed in the propylene oxide reaction step for obvious reasons should be anhydrous so as to prevent hydrolysis of the ester groups.

The starting materials employed for the production of the compounds of this invention are prepared by the following general procedure which for simplicity employs the butyl ester of N-hydroxyphosphinylmethylglycine as the starting reagent.

Butyl-N-(hydroxyphosphinylmethyl)glycine (31.1 g., 0.1488 mole) was dissolved in water (38 ml.) and cooled to 0° C. on an ice bath. Benzylchloroformate (25.35 g., 0.1488 mole) was added and then sodium carbonate (23.65 g., 0.233 mole) was added in small increments over a two-hour period. The solution was allowed to warm to room temperature with continuous stirring. The solution was extracted with diethyl ether and the aqueous portion treated with concentrated hydrochloric acid to a pH of 2. The oily residue which precipitated was extracted with ethyl acetate, washed with water and dried over anhydrous sodium sulfate. The solution was then concentrated in vacuo to yield butyl-N-(hydroxyphosphinylmethyl)-N-(benzyloxycarbonyl)-glycine ($N_D^{25}$=1.5202).

The butyl-N-hydroxyphosphinylmethyl-N-benzyloxycarbonylglycine

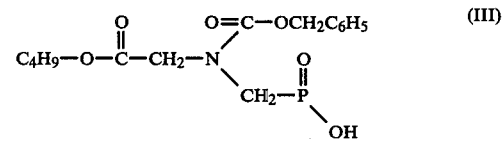

is converted to butyl-N-(bis-chlorophosphinomethyl)-N-(benzyloxycarbonyl)glycine

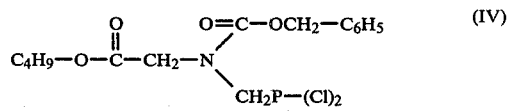

by dissolving in anhydrous benzene and adding dropwise thereto with stirring phosphorus trichloride. After a short period, the solution becomes turbid and is filtered and concentrated in vacuo. The dichloro compound was then dissolved in anhydrous tetrahydrofuran and converted to the butyl ester of N-(diesterphosphinylthioylmethyl)-N-(benzyloxycarbonyl)glycine

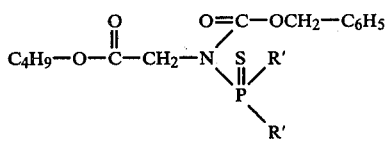

by the following procedure.

A mixture of a thiol or alcohol, e.g., ethanol, ethanethiol, butanethiol and a hydrogen halide acceptor such as triethylamine was then added dropwise to the compound of formula (IV) with stirring over a several hour period. After stirring, sufficient sulfur is added and stirring continued for approximately 16 hours. Sufficient sulfur is at least a molar amount equal to the moles of the phosphorus compound employed. The reaction mixture is then filtered and concentrated to dryness. The N-benzyloxycarbonyl compound is recovered by chromatographing through a silica gel column employing methylene chloride and/or diethyl ester as eluants or by concentration.

The dichloride compound of formula (IV) is extremely unstable and, therefore, it is necessary to employ anhydrous aprotic solvents and anhydrous reactants while protecting the reaction from atmospheric moisture to obtain the best yields of the starting materials.

The reactions in the preparation of the starting materials are generally conducted at ambient temperatures. For convenience, although, higher or lower temperatures can be employed.

The following examples serve to further illustrate the invention. In the examples, all parts are parts by weight unless otherwise expressly set forth.

EXAMPLE 1

Octyl-N-[bis(sec-butanethiol)phosphinothioylmethyl]-N-(benzyloxycarbonyl)glycine (8 g., 0.13 mole) was dissolved in 30 ml. of 35% hydrobromic acid in acetic acid solution containing 1.5 g. of anisole and 30 mg. of ethanedithiol. The reaction was stirred for approximately 2 hours. Ether was added which precipitated a viscous oil. This oil was recovered and washed three times with additional diethyl ether and then taken up in benzene and treated with propylene oxide. The proylene oxide solution was concentrated in vacuo and the residue chromatographed on silica gel employing dichloromethane to give octyl-N-[bis(sec-butanethio)phosphinothioylmethyl]glycine (150 mg.), $N_D^{25} = 1.5320$. The compound gave the following analysis.

Calc'd: C, 51.67; H, 9.13; N, 3.17.
Found: C, 51.07; H, 8.69; N, 2.86.

EXAMPLE 2

Butyl-N-[bis(paramethoxyphenoxy)phosphinothioylmethyl]-N-(benzyloxycarbonyl)glycine (6 g.) was dissolved in 25 ml. of 35% hydrobromic acid in acetic acid solution. The reaction was stirred for approximately 4 hours. Ether was added which precipitated a viscous oil. The oil was recovered and washed three times with more ether. The oil was then dissolved in benzene and treated with excess propylene oxide. The propylene oxide solution was concentrated in vacuo and the resulting oil was chromatographed on silica gel employing ether as an eluant to yield butyl-N-[bis(paramethoxyphenoxy)-phosphinothioylmethyl]glycine (2.5 g.) as an oil, $N_D^{25} = 1.5484$. The compound gave the following analysis.

Calc'd: C, 55.02; H, 6.11; N, 3.05.
Found: C, 54.91; H, 6.21; N, 2.93.

EXAMPLE 3

2-Chloroethyl-N-[bis(2,6-dimethoxyphenoxy)phosphinothioylmethyl]-N-(benzyloxycarbonyl)glycine (14 g.) was dissolved in 30 ml. of 35% hydrobromic acid in acetic acid solution. The reaction was stirred for approximately 3 hours. Ether was added which caused a viscous oil to precipitate. This viscous oil was recovered and washed three more times with additional diethyl ether. The viscous oil was dissolved in benzene and treated with excess propylene oxide. The propylene oxide solution was concentrated in vacuo to give an oil which was chromatographed on silica gel employing ether as an eluant to yield 2-chloroethyl-N-[bis(2,6-dimethoxyphenoxy)phosphinothioylmethyl]glycine as an oil, $N_D^{25} = 1.5615$. The compound gave the following analysis.

Calc'd: C, 48.51; H, 5.23; N, 2.69.
Found: C, 48.69; H, 5.45; N, 2.50.

EXAMPLE 4

2-Chloroethyl-N-[bis(parabromophenylthio)phosphinothioylmethyl]-N-(benzyloxycarbonyl)glycine (8 g.) was dissolved in 30 ml. of 35% hydrobromic acid in acetic acid solution. The reaction was stirred for approximately 3 hours. Ether was added which caused a viscous oil to precipitate. The oil was recovered and washed three times with additional ether. The oil was then dissolved in acetone and crystallized out of the acetone solution with ether, filtered and dried to yield 2-chloroethyl-N-[bis(parabromophenylthio)phosphinothioylmethyl]-glycine having a melting point of 102°–106° C. The compound gave the following analysis.

Calc'd: C, 30.01; H, 2.80; N, 2.06.
Found: C, 29.81; H, 2.95; N, 2.35.

EXAMPLE 5

Ethyl-N-[bis(methylthio)phosphinothioylmethyl]-N-(benzyloxycarbonyl)glycine (5.9 g.) was dissolved in 11 ml. of 35% hydrobromic acid in acetic acid and stirred for one hour. Ether was added to the reaction solution which precipitated ethyl-N-[bis(methylthio)phosphinothioylmethyl]glycine hydrobromide salt as an oily liquid. This oil was washed three more times with additional ether. The material was suspended in benzene and treated with propylene oxide which effected almost complete solution. The solution was then concentrated to an oil at 0.5 torr. The oil thus recovered was chromatographed on 25 g. of silica gel employing diethyl ether as the eluant to yield ethyl-N-[bis(methylthio)-phosphinothioylmethyl]glycine (1.46 g.) as an oil, $N_D^{25} = 1.6002$.

EXAMPLE 6

Ethyl-N-[bis(ethylthio)phosphinothioylmethyl]-N-(benzyloxycarbonyl)glycine (4.0 g.) was dissolved in 10 ml. of 35% hydrobromic acid in acetic acid and stirred for one hour. Ether was then added to precipitate the desired material as the hydrobromide salt. The residue was washed three additional times with ether. The residue was then dissolved in benzene and treated with excess propylene oxide. The propylene oxide-benzene solution was then concentrated in vacuo to yield a yellow oil (1.5 g.) which was chromatographed on fluorosil with diethyl ether as an eluant to yield ethyl-N-[bis(ethylthio)phosphinothioylmethyl]glycine as an oil, $N_D^{25}=1.582$.

EXAMPLE 7

Ethyl-N-[bis(phenylthio)phosphinothioylmethyl]-N-(benzyloxycarbonyl)glycine (2.3 g.) was dissolved in 10 ml. of 35% hydrobromic acid in acetic acid and stirred for approximately one hour. Diethyl ether was added to precipitate the hydrobromide salt of the desired compound. The hydrobromide salt was washed an additional three times with diethyl ether. The oily residue was then dissolved in benzene and treated with excess propylene oxide and the resulting solution concentrated in vacuo to yield ethyl-N-[bis(phenylthio)phosphinothioylmethyl]-glycine as an oil, $N_D^{25}=1.413$.

EXAMPLE 8

Ethyl-N-[bis(isopropylthio)phosphinothioylmethyl]-N-(benzyloxycarbonyl)glycine (4.0 g.) was dissolved in 10 ml. of 35% hydrobromic acid in acetic acid for one hour. Diethyl ether was added and a viscous oil precipitated. The ether was decanted and the precipitate washed with diethyl ether an additional three times. The precipitate was dissolved in acetonitrile and excess propylene oxide added. After about 5 minutes, the solution was concentrated in vacuo to yield ethyl-N-[bis-(isopropylthio)phosphinothioylmethyl]glycine (0.95 g.) as an oil, $N_D^{25}=1.5524$. The compound gave the following analysis.

Calc'd: C, 40.10; H, 7.34; N, 4.25.
Found: C, 40.30; H, 7.31; N, 4.33.

EXAMPLE 9

Ethyl-N-[bis(isobutylthio)phosphinothioylmethyl]-N-(benzyloxycarbonyl)glycine (4.0 g.) was mixed with 10 ml. of 35% hydrobromic acid in acetic acid and stirred for 45 minutes. Diethyl ether (100 ml.) was added which precipitated out the desired product as a hydrobromide salt as an oil. The ether was discarded and the oily precipitate was washed an additional three times with diethyl ether. The precipitate was then dissolved in benzene and treated with excess propylene oxide. The propylene oxide treated solution was concentrated to an oily residue which was chromatographed on silica gel employing acetonitrile as an eluant to yield ethyl-N-[bis(isobutylthio)-phosphinothioylmethyl]glycine as an oil, $N_D^{25}=1.5451$, which gave the following analysis.

Calc'd: C, 43.80; H, 7.63; N, 3.93.
Found: C, 43.87; H, 7.53; N, 3.98.

EXAMPLE 10

Ethyl-N-[bis(metachlorophenoxy)phosphinothioylmethyl]-N-(benzyloxycarbonyl)glycine (1.0 g.) was dissolved in 15 ml. of 35% hydrobromic acid in acetic acid and was stirred for one hour. The reaction mixture was concentrated under vacuum and the residue triturated thoroughly with ether three times, dissolved in benzene and treated with excess propylene oxide. The resultant solution was concentrated in vacuo and the residue chromatographed on silica gel using diethyl ether as an eluant to yield ethyl-N-[bis(metachlorophenoxy)phosphinothioylmethyl]glycine as an oil, $N_D^{25}=1.5371$, which gave the following analysis.

Calc'd: C, 47.02; H, 4.18; N, 3.23.
Found: C, 47.86; H, 4.44; H, 3.04.

EXAMPLE 11

Ethyl-N-[bis(n-butylthio)phosphinothioylmethyl]-N-(benzyloxycarbonyl)glycine (3.1 g.) was dissolved in 15 ml. of 35% hydrobromic acid in acetic acid and stirred for two hours. The solvent was then removed under reduced pressure and the residue triturated four times with diethyl ether. The residue was then dissolved in benzene, treated with excess propylene oxide and concentrated to a viscous oil. The viscous oil was chromatographed on silica gel employing dichloromethane to yield ethyl-N-[bis(n-butylthio)phosphinothioylmethyl]glycine as an oil, $N_D^{25}=1.4835$.

EXAMPLE 12

2-Ethoxyethyl-N-[bis(butylthio)phosphinothioylmethyl]-N-(benzyloxycarbonyl)glycine (9.2 g., 0.017 mole) was dissolved in 30 ml. of 35% hydrobromic acid in acetic acid. The reaction was stirred for approximately 6 hours. Diethyl ether was added which precipitated a viscous oil. The oil was washed three additional times with diethyl ether and then dissolved in benzene. The benzene solution was treated with excess propylene oxide. The propylene oxide treated solution was concentrated in vacuo and the residue chromatographed on silica gel employing diethyl ether as an eluant to yield 2-ethoxyethyl-N-[bis(butylthio)phosphinothioylmethyl]glycine as an oil, $N_D^{25}=1.5490$, which gave the following analysis.

Calc'd: C, 43.94; H, 8.05; n, 3.41.
Found: C, 44.27; H, 7.85; N, 3.18.

The strong acid salts of compounds of formula (I) are produced by dissolving the compound in a suitable anhydrous solvent such as benzene, chloroform, methylene chloride, diethyl ether and adding an anhydrous strong acid. The salt precipitated as a solid or insoluble oil. The hydrobromide salt is, of course, produced during the hydrolysis of the N-benzyloxycarbonyl group.

The strong acids which can be employed to produce the strong acid salts of the compounds of formula (I) are those which have a $pK_a$ of 2.2 or less as measured in aqueous solution. Acid having a $pK_a$ of as low as 0.1 or even lower can be employed. Examples of such acids are hydrochloric, hydrobromic, hydroiodic, sulfuric acid, chlorosulfonic, methane sulfonic, benzene sulfonic, trichloroacetic, trifluoroacetic, pentafluoropropionic, heptafluorobutyric, trifluoromethane sulfonic acid, oxalic acid and the like.

The following examples show the preparation of strong acid salts other than the hydrobromic salt which is formed in the process of producing the compounds of this invention which are not strong acid salts.

EXAMPLE 13

Ethyl-N-(diphenoxyphosphinothioylmethyl)glycine was dissolved in benzene and methane sulfonic acid added. Diethyl ether was added and the methane sulfonic acid salt precipitated as a white solid, m.p. 81°–84° C.

EXAMPLE 14

Ethyl-N-(diphenoxyphosphinothioylmethyl)glycine was dissolved in anhydrous ethanol and saturated with dry hydrogen chloride. The ethanol solution was concentrated to dryness to yield an oil. Diethyl ether was added and the mixture stirred overnight. The ether was decanted, methylene chloride added and the solution filtered. The solution was evaporated to dryness. The residue was dissolved in benzene, diethyl ether added to the cloud point and crystallization began. The hydrochloride salt of ethyl-N-(diphenoxyphosphinothioylmethyl)glycine was collected as a white solid having a melting point of 98°–102° C.

EXAMPLE 15

Ethyl-N-(diphenoxyphosphinothioylmethyl)glycine was dissolved in dry benzene and a concentrated ethanolic solution of oxalic acid was added. The solid which formed was collected by filtration and air dried. The solid was dissolved in hot chloroform, diethyl ether was added and the solution cooled to yield the oxalic acid salt of ethyl-N-(diphenoxyphosphinothioylmethyl)glycine as a white solid, m.p. 150°–151° C.

EXAMPLE 16

The post-emergence herbicidal activity of the various compounds of this invention is demonstrated by greenhouse testing in the following manner. A good grade of top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with soil and leveled. The pans are then placed on a sand bench in the greenhouse and watered from below as needed. After the plants reach the desired age (two to three weeks), each pan except for the control pans is removed individually to a spraying chamber and sprayed by means of an atomizer operating at a positive air pressure of approximately 1.46 kg/cm$^2$ absolute. The atomizer contains 6 ml. of a solution or suspension of the chemical and an amount of a cyclohexanone emulsifying agent mixture so that the spray solution or suspension contains about 0.4% by weight of the emulsifier. The spray solution or suspension contains a sufficient amount of the candidate chemical in order to give application rates corresponding to those set forth in the tables. The spray solution is prepared by taking an aliquot of a 1.0% by weight stock solution or suspension of the candidate chemical in an organic solvent such as acetone or tetrahydrofuran or in water. The emulsifying agent employed is a mixture comprising 35 weight percent butylamine dodecylbenzene sulfonate and 65 weight percent butylamine dodecylbenzene sulfonate and 65 weight percent of a tall oil ethylene oxide condensate having about 11 moles of ethylene oxide per mole of tall oil. The pans are returned to the greenhouse and watered as before and the injury to the plants as compared to the control is observed at approximately two and four weeks as indicated in the tables under WAT and the results recorded. In some instances, the four-week observations are omitted.

The post-emergence herbicidal activity index used in Tables I and II is as follows:

| Plant Response | Index |
| --- | --- |
| 0–24% control | 0 |
| 25–49% control | 1 |
| 50–74% control | 2 |
| 75–99% control | 3 |
| 100% control | 4 |

The plant species utilized in these tests are identified by letter in accordance with the following legend:

| | |
| --- | --- |
| A - Canada Thistle* | K - Barnyardgrass |
| B - Cocklebur | L - Soybean |
| C - Velvetleaf | M - Sugar Beet |
| D - Morningglory | N - Wheat |
| E - Lambsquarters | O - Rice |
| F - Smartweed | P - Sorghum |
| G - Yellow Nutsedge* | Q - Wild Buckwheat |
| H - Quackgrass* | R - Hemp Sesbania |
| I - Johnsongrass* | S - Panicum Spp |
| J - Downy Brome | T - Crabgrass |

*Established from vegetative propagules.

Table I

| Compound of Example No. | WAT | kg h | \multicolumn{11}{c}{Post-Emergent Plant Species} |
| --- | --- | --- | --- | --- | --- | --- | --- | --- | --- | --- | --- | --- | --- |
| | | | A | B | C | D | E | F | G | H | I | J | K |
| 1 | 5 | 33.6 | 0 | 1 | 0 | 1 | 3 | 0 | 1 | 1 | 1 | 1 | 1 |
| 2 | 4 | 11.2 | 0 | 0 | 0 | 1 | 0 | 2 | 2 | 1 | 0 | 0 | 2 |
| 2 | 4 | 5.6 | 0 | 1 | 0 | 1 | 1 | 0 | 0 | 0 | 0 | 0 | 2 |
| 3 | 4 | 11.2 | 1 | 1 | 1 | 1 | 1 | 2 | 2 | 1 | 2 | 0 | 3 |
| 3 | 4 | 5.6 | 0 | 0 | 0 | 0 | 0 | 1 | 1 | 0 | 0 | 0 | 2 |
| 4 | 4 | 11.2 | 2 | 2 | 1 | 2 | 1 | 3 | 1 | 2 | 0 | 3 | 3 |
| 4 | 4 | 5.6 | 0 | 1 | 0 | 1 | 0 | 0 | 1 | 0 | 0 | 0 | 1 |
| 5 | 4 | 11.2 | 1 | 3 | 2 | 2 | 4 | 4 | 2 | 3 | 1 | 2 | 3 |
| 5 | 4 | 5.6 | 1 | 1 | 1 | 1 | 2 | 2 | 1 | 2 | 2 | 1 | 2 |
| 6* | 4 | 11.2 | 1 | 1 | 3 | 3 | 4 | 3 | 2 | 3 | 1 | 3 | 3 |
| 6 | 4 | 5.6 | 1 | 2 | 3 | 2 | 4 | 3 | 2 | 2 | 4 | 2 | 2 |
| 7 | 4 | 11.2 | 2 | 2 | 1 | 2 | 3 | 1 | 0 | 1 | 0 | 0 | 3 |
| 7 | 4 | 5.6 | 0 | 2 | 0 | 1 | 2 | 0 | 0 | 0 | 0 | 0 | 2 |
| 8 | 4 | 11.2 | 1 | 1 | 1 | 1 | 0 | 3 | 1 | 1 | 3 | 1 | 3 |
| 8 | 4 | 5.6 | 0 | 2 | 1 | 1 | 1 | 1 | 1 | 1 | 1 | 0 | 1 |
| 9 | 4 | 11.2 | 1 | 3 | 2 | 2 | 2 | 1 | 1 | 1 | 2 | 2 | 3 |
| 9 | 4 | 5.6 | 0 | 3 | 2 | 1 | 1 | 2 | 2 | 1 | 2 | 1 | 3 |
| 12 | 5 | 11.2 | 1 | 1 | 0 | 0 | 1 | 0 | 0 | 0 | 0 | 0 | 1 |
| 12 | 2 | 5.6 | 0 | 0 | 0 | 1 | 0 | 0 | 0 | 0 | 0 | 0 | 1 |
| 13 | 4 | 11.2 | 1 | 2 | 1 | 2 | 4 | 1 | 1 | 3 | 3 | 1 | 3 |
| 13 | 4 | 5.6 | 1 | 2 | 2 | 2 | 3 | 2 | 1 | 1 | 2 | 1 | 3 |
| 14 | 4 | 11.2 | 3 | 3 | 3 | 1 | 4 | 3 | 3 | 4 | 3 | 1 | 4 |
| 14 | 4 | 5.6 | 3 | 3 | 1 | 1 | 4 | 4 | 2 | 2 | 2 | 1 | 4 |
| 15 | 4 | 11.2 | 4 | 3 | 3 | 3 | 4 | 4 | 2 | 3 | 3 | 3 | 4 |
| 15 | 4 | 5.6 | 1 | 3 | 2 | 2 | 4 | 4 | 3 | 3 | 2 | 1 | 4 |

*Formulated just prior to spraying.

The compounds of Example Numbers 13, 14 and 15 were further tested in a secondary test against the weed species shown in Table II.

Table II

| Compound of Example No. | WAT | kg h | Post-Emergent Plant Species | | | | | | | | | | | | | | |
|---|---|---|---|---|---|---|---|---|---|---|---|---|---|---|---|---|---|
| | | | L | M | N | O | P | B | Q | D | R | E | F | C | J | S | K | T |
| 13 | 4 | 5.6  | 1 | 3 | 4 | — | 2 | 3 | 2 | 2 | 2 | 4 | 3 | 3 | 2 | 4 | 4 | 4 |
| 13 | 4 | 1.12 | 1 | 1 | 1 | 1 | 2 | 1 | 0 | 1 | 1 | 2 | 2 | 1 | 2 | 3 | 3 | 3 |
| 13 | 4 | 0.28 | 0 | 0 | 0 | 0 | 1 | 2 | 1 | 2 | 1 | 1 | 1 | 1 | 0 | 3 | 2 | 3 |
| 14 | 4 | 5.6  | 1 | 3 | 3 | 2 | 2 | 2 | 1 | 1 | 1 | 4 | 3 | 3 | 1 | 4 | 3 | 3 |
| 14 | 4 | 1.12 | 1 | 0 | 1 | 1 | 1 | 2 | 1 | 1 | 1 | 3 | 2 | 1 | 0 | 3 | 3 | 3 |
| 14 | 4 | 0.28 | 0 | 0 | 1 | 2 | 1 | 0 | 1 | 1 | 2 | — | 1 | 1 | 0 | 2 | 2 | 2 |
| 15 | 4 | 5.6  | 1 | 1 | 3 | 1 | 2 | 1 | 1 | 1 | 3 | 4 | 3 | — | 1 | 3 | 3 | 3 |
| 15 | 4 | 1.12 | 1 | 0 | 1 | 1 | 1 | 1 | 1 | 1 | 1 | 3 | 1 | — | 1 | 2 | 2 | 3 |
| 15 | 4 | 0.28 | 1 | 0 | 0 | 0 | 1 | 0 | 0 | 1 | 1 | 2 | 0 | — | 0 | 1 | 1 | 2 |

From the test results presented in Tables I and II, it can be seen that the post-emergent herbicidal activity of the compounds of this invention is, for the most part, general in nature. In certain specific instances, however, some selectivity is demonstrated. In this regard, it should be recognized that each individual speciees selected for the above tests is a representative member of a recognized family of plant species.

The Herbicidal compositions, including concentrates which require dilution prior to application to the plants, of this invention contain from 5 to 95 parts by weight of at least one compound of this invention and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, acetone, tetrahydrofuran, all parts being by weight of the total composition. Preferably, the compositions of this invention contain from 5 to 75 parts by weight of at least one compound of this invention, together with the adjuvants. Where required, from about 0.1 to 2.0 parts by weight of the inert liquid extender can be replaced by a corrosion inhibitor or anti-foaming agent, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid or organic origin, water, a wetting agent, a dispersing agent, an emulsifying agent or any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surfaceactive agent into the compositions greatly enhances their efficacy. By the term "surface-active agent," it is understood that wetting agents, dispersing agents, suspending agents and emulsifying agents are included therein. Anionic, cationic and nonionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin, sulfonates, polymeric alkyl naphthalene sulfonates, sodium naphthalene sulfonate, polymethylene bisnaphthalenesulfonate and sodium N-methyl-N-(long chain acid) taurates.

When operating in accordance with the present invention, effective amounts of the compounds or compositions of this invention are applied to the plants, or to soil containing the plants, or are incorporated into aquatic media in any convenient fashion. The application of liquid and particulate solid compositions to plants or soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media to the area where control of the aquatic plants is desired.

The application of an effective amount of the compounds or compositions of this invention to the plant is essential and critical for the practice of the present invention. The exact amount of active ingredient to be employed is dependent upon the response disired in the plant as well as such other factors as the plant species and stage of development thereof, and the amount of rainfall as well as the specific glycine employed. In foliar treatment for the control of vegetative growth, the active ingredients are applied in amounts from about 0.112 to about 22.4 or more kilograms per hectare. In pre-emergent treatments, the rate of application can be from about 11.2 to about 22.4 or more kilograms per hectare. In applications for the control of aquatic plants, the active ingredients are applied in amounts of from about 0.01 parts per million to about 1000 parts per million, based on the aquatic medium. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound of the formula

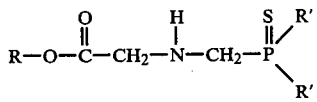

wherein R is a member of the class consisting of alkyl of from 1 to 10 carbon atoms, chloroalkyl of from 1 to 4 carbon atoms and from 1 to 3 chlorine atoms and alkoxyalkyl groups containing from 3 to 7 carbon atoms and each R' is a member of the class consisting of thioalkyl of from 1 to 6 carbon atoms, phenoxy, phenylthio and said phenoxy and phenylthio groups substituted with from 1 to 2 members of the class consisting of halo, lower alkyl of from 1 to 4 carbon atoms and lower alkoxy of from 1 to 4 carbon atoms and the strong acid salts thereof.

2. A compound of claim 1 wherein R is alkyl of from 1 to 4 carbon atoms.

3. A compound of claim 2 wherein R is ethyl.

4. A compound of claim 2 wherein R' is methylthio.

5. A compound of claim 2 wherein R' is ethylthio.

6. A compound of claim 2 wherein R' is sec-butylthio.

7. A compound of claim 1 wherein R is chloroethyl.

8. A compound of claim 2 which is the strong acid salt.

9. A compound of claim 3 which is the strong acid salt.

10. A compound of claim 9 wherein R' is phenoxy and the strong acid is methane sulfonic acid.

11. A compound of claim 1 wherein R' is phenoxy and the strong acid is hydrogen chloride.

12. A compound of claim 1 wherein R' is phenoxy and the strong acid is oxalic acid.

13. A herbicidal composition comprising a herbicidally effective amount of a compound of claim 1 together with an inert diluent.

14. A herbicidal composition comprising a herbicidally effective amount of a compound of claim 2 together with an inert diluent.

15. A herbicidal composition comprising a herbicidally effective amount of a compound of claim 3 together with an inert diluent.

16. A herbicidal composition comprising a herbicidally effective amount of a compound of claim 4 together with an inert diluent.

17. A herbicidal composition comprising a herbicidally effective amount of a compound of claim 5 together with an inert diluent.

18. A herbicidal composition comprising a herbicidally effective amount of a compound of claim 6 together with an inert diluent.

19. A herbicidal composition comprising a herbicidally effective amount of a compound of claim 7 together with an inert diluent.

20. A herbicidal composition comprising a herbicidally effective amount of a compound of claim 8 together with an inert diluent.

21. A herbicidal composition comprising a herbicidally effective amount of a compound of claim 9 together with an inert diluent.

22. A herbicidal composition comprising a herbicidally effective amount of a compound of claim 10 together with an inert diluent.

23. A herbicidal composition comprising herbicidally effective amount of a compound of claim 11 together with an inert diluent.

24. A herbicidal composition comprising a herbicidally effective amount of a compound of claim 12 together with an inert diluent.

25. A herbicidal method which comprises contacting a plant with a herbicidally effective amount of a compound of claim 1.

26. A herbicidal method which comprises contacting a plant with a herbicidally effective amount of a compound of claim 2.

27. A herbicidal method which comprises contacting a plant with a herbicidally effective amount of a compound of claim 3.

28. A herbicidal method which comprises contacting a plant with a herbicidally effective amount of a compound of claim 4.

29. A herbicidal method which comprises contacting a plant with a herbicidally effective amount of a compound of claim 5.

30. A herbicidal method which comprises contacting a plant with herbicidally effective amount of a compound of claim 6.

31. A herbicidal method which comprises contacting a plant with a herbicidally effective amount of a compound of claim 7.

32. A herbicidal method which comprises contacting a plant with a herbicidally effective amount of a compound of claim 8.

33. A herbicidal method which comprises contacting a plant with a herbicidally effective amount of a compound of claim 9.

34. A herbicidal method which comprises contacting a plant with a herbicidally effective amount of a compound of claim 10.

35. A herbicidal method which comprises contacting a plant with a herbicidally effective amount of a compound of claim 11.

36. A herbicidal method which comprises contacting a plant with a herbicidally effective amount of a compound of claim 12.

* * * * *